(12) United States Patent
Ehara et al.

(10) Patent No.: US 7,319,028 B2
(45) Date of Patent: Jan. 15, 2008

(54) **PROCESS FOR PRODUCING SPORANGIA OF *BACILLUS POPILLIAE*, CONTROL AGENT, AND CONTROLLING METHOD**

(75) Inventors: Gaku Ehara, Sakura (JP); Masaharu Kimura, Ichihara (JP); Hideji Nishihashi, Sakura (JP); Tomoko Yokoyama, Chiba (JP); Makoto Hasegawa, Chiba (JP); Masao Tanaka, Chiba (JP); Azusa Fujiie, Chousei-gun (JP); Shinichi Aoyagi, Katori-gun (JP)

(73) Assignees: Dainippon Ink and Chemicals, Inc., Tokyo (JP); Chiba Prefectural Government, Chiba-shi (JP)

( * ) Notice: Subject to any disclaimer, the term of this patent is extended or adjusted under 35 U.S.C. 154(b) by 0 days.

(21) Appl. No.: 10/730,258

(22) Filed: Dec. 9, 2003

(65) Prior Publication Data

US 2005/0123518 A1   Jun. 9, 2005

(51) Int. Cl.
| | |
|---|---|
| *C12N 9/00* | (2006.01) |
| *C12N 3/00* | (2006.01) |
| *C12N 1/00* | (2006.01) |
| *C12N 1/38* | (2006.01) |
| *C12N 1/36* | (2006.01) |
| *C12N 1/26* | (2006.01) |
| *C12N 1/12* | (2006.01) |
| *C12N 1/20* | (2006.01) |
| *C12N 1/22* | (2006.01) |
| *A61K 39/07* | (2006.01) |
| *A01N 63/00* | (2006.01) |

(52) U.S. Cl. ................ 435/183; 435/242; 435/243; 435/244; 435/245; 435/248; 435/252.1; 435/252.5; 435/252; 435/252.31; 424/246.1; 424/93.46

(58) Field of Classification Search ............... 435/243, 435/244, 245, 248, 252.1, 252.2, 252, 252.5, 435/242, 252.31, 183; 424/246.1, 93.46
See application file for complete search history.

(56) References Cited

U.S. PATENT DOCUMENTS 4,824,671 A   4/1989   Ellis et al. .................. 424/195

2006/0090220 A1 *   4/2006   Tanaka et al. ............. 800/279

FOREIGN PATENT DOCUMENTS

| JP | 411332556 A | * 12/1999 |
|---|---|---|
| JP | 2001-149066 | 6/2001 |
| JP | 2002-355030 | * 10/2002 |
| JP | 2002-355030 | 12/2002 |

OTHER PUBLICATIONS

Haynes et al (Sporogenicity of yeast autolyzates casein hydrolyzates for *Bacillus popilliae* in liquid cultures, Journal of Invertebrate Pathology, 1973; 22: 377-81).*

Theunis et al (Journal of Invertebrate Pathology, 1999; 73: 255-259).*

Pettersson et al; "Transfer of *Bacillus lentimorbus* and *Bacillus popilliae* to the genus *Paenibacillus* with emended descriptions of *Paenibacillus lentimorbus* comb. Nov. and *Paenibacillus popilliae* comb. Nov." Int'l Journal of Systematic Bacteriology (1999); 49, pp. 531-540.

Fukuhara, T. Konchuu Byourigaku (1991); Insect Pathology, pp. 54-59; with partial English translation.

Haynes et al; "Sporogenicity of Yeast Autolyzates and Casein Hydrolyzates for *Bacillus popilliae* in Liquid Cultures"; J. Invertebrate Pathology (1973); 22, pp. 377-381.

Haynes et al; "Sporulation of *Bacillus popilliae* in Liquid Cultures"; J. Invertebrate Pathology (1972); 19, pp. 125-130.

Co-pending U.S. Appl. No. 10/743,546, filed Dec. 23, 2003; entitled: "Process for Producing Sporangia of Bacillus Popilliae".

* cited by examiner

*Primary Examiner*—Robert A. Zeman
*Assistant Examiner*—Lakia J Tongue
(74) *Attorney, Agent, or Firm*—Edwards Angell Palmer & Dodge LLP (57) ABSTRACT

The present invention provides a process for efficiently producing sporangia of *Bacillus popilliae* containing spores and parasporal bodies having controlling effects on *Scarabaeidae* insects, and a control agent and controlling method for *Scarabaeidae* insects obtained by said production process. In a process for producing sporangia of *Bacillus popilliae* containing spores and parasporal bodies by culturing *Bacillus popilliae* in a medium containing an adsorbent, the medium contains 0.2-4.0% by weight of glutamic acid.

3 Claims, 2 Drawing Sheets

PROCESS FOR PRODUCING SPORANGIA OF *BACILLUS POPILLIAE*, CONTROL AGENT, AND CONTROLLING METHOD

BACKGROUND OF THE INVENTION

1. Field of the Invention

The present invention relates to a process for producing sporangia of microorganisms belonging to *Bacillus popilliae* containing spores and parasporal bodies use as control agents of *Scarabaeidae* insects ("sporangia containing spores and parasporal bodies" may simply be referred to as "sporangia").

2. Description of the Related Art

The larva of *Scarabaeidae* insects feed on a wide range of plant roots such as those of grasses, agricultural and horticultural crops and trees, and are known to cause considerable damage. Since these larva live underground, in addition to it being difficult to identify the locations where these larva are present, a high degree of control effects are unable to be obtained even if agricultural chemicals are sprayed from the air. Therefore, in order to demonstrate remarkable effects, it has been necessary to spray large amounts of agricultural chemicals over a wide range to enable the chemicals to penetrate into the ground. However, since there are concerns over this method having a detrimental effect on both the natural environment and people, a more effective control method is desired.

Microorganisms belonging to *Bacillus popilliae* are known to parasitically cause milky disease in the larva of *Scarabaeidae* insects, eventually cause their death. Attempts have long been made to use the sporangia of these microorganisms to control *Scarabaeidae* insects on which agricultural chemicals have little effect. However, although these microorganisms grow within the larva of *Scarabaeidae* insects, it is difficult to grow them by culturing using artificial media, and the production of sporangia of these microorganisms in media has been particularly difficult. In addition, Fukuhara reported that infection and pathogenesis of larva do not occur with sporangia obtained by culturing using conventional media (Fukuhara, T., ed., Insect Pathology, p. 57, 1979). Namely, there has yet to be an efficient method for large-volume production of these sporangia that can be used effectively for control of *Scarabaeidae* insects.

For example, Haynes, et al. reported an example of obtaining a maximum of $2.06\times10^{7}$ sporangia per 1 ml of liquid culture by attempting to culture microorganisms belonging to *Bacillus popilliae* in liquid medium containing 0.5% peptone, 1.5% yeast extract, 0.3% dipotassium hydrogenphosphate, 0.1% glucose and 1% activated carbon (Journal of Invertebrate Pathology, Vol. 22, p. 377-381, 1973). However, the ratio of the content of glutamic acid to the medium and the ratio of the content of glutamic acid to total amino acids are unclear. In addition, Haynes, et al. also described in the same report that amino acid composition is unrelated to production of sporangia (p. 379, column 1, line 19).

In addition, Haynes, et al. reported that $3.1\times10^{7}$ sporangia per 1 ml of liquid culture were obtained by culturing mature cells of *Bacillus popilliae* in the late logarithmic increase stage in liquid medium containing 0.5% peptone (tryptone), 1.5% yeast extract, 0.3% dipotassium hydrogenphosphate, 0.1% glucose and 1% activated carbon (Journal of Invertebrate Pathology, Vol. 19, p. 125-130, 1972). However, this culturing method has a long culturing time, taking roughly two weeks.

In addition, an example of having obtained $1\times10^{9}$ spores per 1 ml of liquid culture by culturing in liquid medium containing 1% soluble starch, 0.1% trehalose, 0.5% yeast extract, 0.3% dipotassium hydrogenphosphate and 0.1% calcium carbonate is indicated in the specification of U.S. Pat. No. 4,824,671. However, in this case as well, the resulting spores were not accompanied by parasporal bodies, and the rate of infection with milky disease when spores were sprayed at the rate of $2.0\times10^{12}$ spores per 1 kg of soil and allowed to be orally ingested by larva of *Scarabaeidae* insects for 7 weeks was 47.50%, indicating weak insecticidal effects on larva of *Scarabaeidae* insects even when compared with sporangia formed within the bodies of the larva.

BRIEF SUMMARY OF THE INVENTION

The object of the present invention is to provide a process for efficiently obtaining sporangia of microorganisms belonging to *Bacillus popilliae* containing spores and parasporal bodies that are effective in controlling *Scarabaeidae* insects, and a control agent for *Scarabaeidae* insects obtained by said production process, and a controlling method.

As a result of conducting extensive research to solve the aforementioned problems, the inventors of the present invention found that sporangia of microorganisms belonging to *Bacillus popilliae* containing spores and parasporal bodies are efficiently obtained by culturing in a medium to which glutamic acid and an adsorbent which is thought to remove growth inhibiting substances have been added at specific concentrations, thereby leading to completion of the present invention.

Namely, in order to solve the aforementioned problems, the present invention provides a process for producing sporangia of *Bacillus popilliae* containing spores and parasporal bodies by culturing *Bacillus popilliae* in a medium containing an adsorbent and 0.2-4.0% by weight of glutamic acid.

In addition, the present invention provides a control agent for *Scarabaeidae* insects containing as active ingredient sporangia of *Bacillus popilliae* containing spores and parasporal bodies obtained by the aforementioned production process, and a controlling method for *Scarabaeidae* insects comprising spraying said control agent on soil where *Scarabaeidae* insects live.

According to the production process of the present invention, sporangia of *Bacillus popilliae* containing spores and parasporal bodies can be produced in high yield. In addition, since the sporangia of *Bacillus popilliae* containing spores and parasporal bodies obtained by the production process of the present invention exhibit control effects such as insecticidal and growth inhibitory effects on the larva of insects, and of *Scarabaeidae* insects in particular, it is useful as a control agent and controlling method for these insects.

BRIEF DESCRIPTION OF THE DRAWINGS

FIG. 1 is a schematic drawing showing a sporangium of *Bacillus popilliae* containing a spore and a parasporal body.

FIG. 2 is a schematic drawing of a high-performance liquid chromatography system used for amino acid analysis.

FIG. 3 is a graph showing the number of sporangia and the number of microbial cells versus the concentration of glutamic acid in media used in Examples 4-8 and Comparative Examples 9-10.

DETAILED DESCRIPTION OF THE PREFERRED EMBODIMENTS

The following provides a detailed explanation of the present invention.

According to Bergey's Manual of Determinative Bacteriology, Eighth Edition, the bacteriological properties of the microorganisms belonging to *Bacillus popilliae* used in the present invention consist of morphological properties including being Gram negative bacilli having a length of 1.3-5.2 μm and width of 0.5-0.8 μm, a growth temperature of 20-35° C., and the sporangia having a spore and parasporal body inside.

Figure 1:
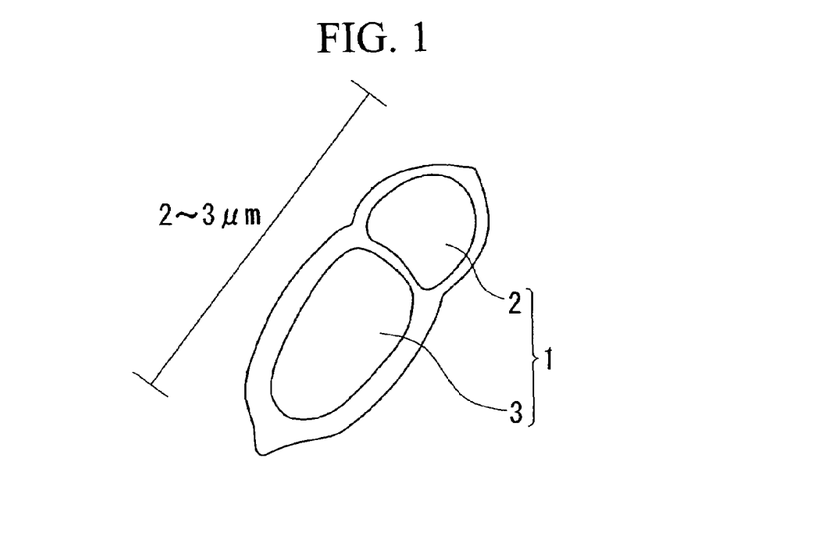
Figure 2:
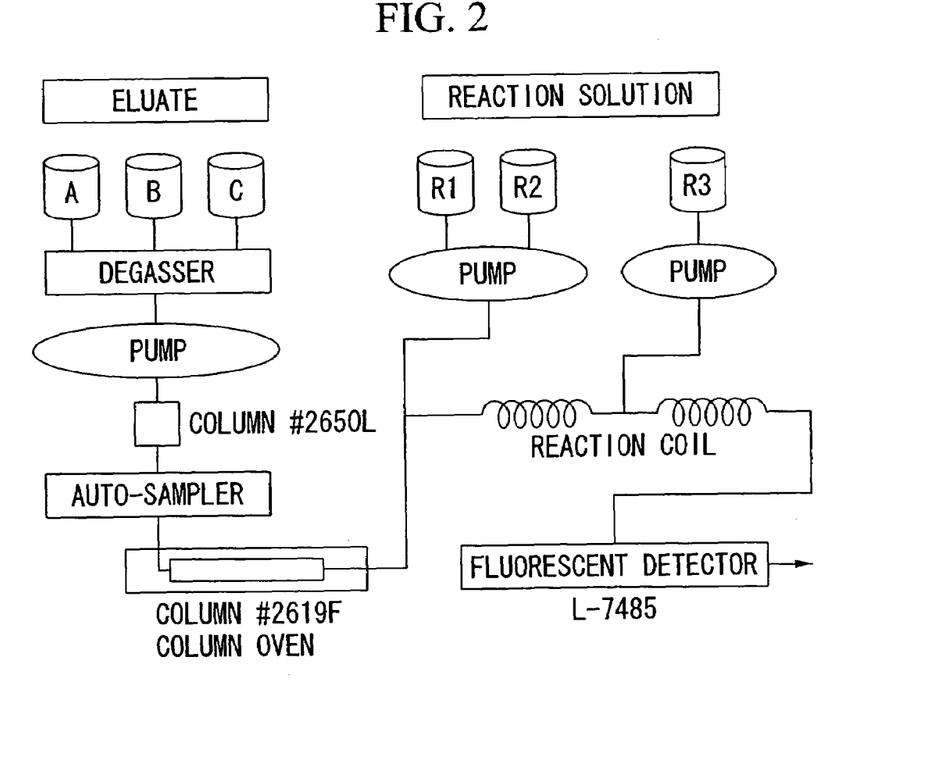

As shown in the schematic drawing of FIG. 1, sporangium 1 of *Bacillus popilliae* is a capsule containing a spore 3 and a small body referred to as a parasporal body 2 (or parasporal cell). However, according to literature relating to culturing methods of *Bacillus popilliae* using conventional media, there are many examples in which sporangia and spores are used without a clear distinction, and it was often unclear as to whether the term "spore" in the literature referred to the spore alone, sporangia that contained a spore only, or sporangia that contained a spore and a parasporal body. The inventors of the present invention clearly determined that both the spore and parasporal body are required in order to obtain control effects resulting from insecticide or growth inhibition on larva of insects, and particularly those of *Scarabaeidae* insects.

It has recently been proposed, based on the theoretical opinions of Pettersson, et al. (Int. J. Syst. Bacteriol., Vol. 49, p. 531-540, 1999), that *Bacillus popilliae*, including strains that have been classified thus far, should be reclassified as *Paenibacillus popilliae*. In addition, Rippere, et al. (Int. J. Syst. Bacteriol., Vol. 48, p. 395-402, 1998) and Harrison, et al. (J. Invertebr. Pathol., Vol. 76, p. 169-175, 2000) have proposed that the milky disease pathogens of *Bacillus popilliae* and *Bacillus lentimorbus* be classified at the DNA level since they cannot be clearly distinguished on the basis of only the presence or absence of parasporal bodies and the presence or absence of growth in 2% salt-containing medium, which had been used to distinguish the two species in the past. Since there classification is not clearly defined at present, the microorganisms belonging to *Bacillus popilliae* in the present invention are to include microorganisms belonging to *Paenibacillus popilliae* and microorganisms belonging to *Paenibacillus lentimorbus*.

The medium used in the production process of the present invention contains an adsorbent for the purpose of removing substances that inhibit the growth of sporangia. Examples of said adsorbent include activated carbon, adsorbent resin, allophosite and molecular sieve. Since hydrogen peroxide is considered to be the main substance that inhibits the growth of sporangia, the adsorbent preferably has the ability to decompose or eliminate hydrogen peroxide, and a specific example of a preferable adsorbent is activated carbon.

Although the activated carbon used for the adsorbent may be in the form of a powder, granules or a sheet and so forth, powdered activated carbon is particularly preferable because it is superior in terms of the growth efficiency and sporangia formation rate of the microorganisms.

Adsorbent resin used for the absorbent refers to porous polymers that adsorb microscopic substances, examples of which include crosslinked porous polymers molded into granules which function as a synthetic resin capable of efficiently adsorbing microscopic substances in aqueous solution due to the microporous structure that extends inside the granules. Specific examples include the aromatic synthetic resin adsorbents manufactured by Mitsubishi Chemical under the trade names of Diaion HP20, Diaion HP21, Sepabeads SP825, Sepabeads SP850, Sepabeads SP70 and Sepabeads SP700, the substituted aromatic synthetic resin adsorbent manufactured by Mitsubishi Chemical under the trade name of Sepabeads SP207, and the acrylic synthetic resin adsorbent also manufactured by Mitsubishi Chemical under the trade name of Diaion HP2MG.

Although there are no particular restrictions on the concentration of adsorbent in the medium used in the production process of the present invention provided it is within a range for which the effects of the present invention are achieved, it is preferably 0.05-5% by weight relative to the medium. By making the concentration of adsorbent in the medium 0.05% by weight or more, adsorption and elimination effects on substances that inhibit microorganism growth can be adequately demonstrated, and by making the concentration of adsorbent in the medium 5% by weight or less, the adsorption of nutrient sources required for growth of the microorganisms can be minimized, thereby resulting in the superior microbial growth promotional effects being demonstrated within the aforementioned range. The adsorbent may be added to the medium prior to sterilization, may be sterilized together with the medium, or that which has been sterilized separately may be added to the medium following sterilization.

The glutamic acid contained in the medium used in the production process of the present invention also includes physiologically acceptable salts thereof, specific examples of which include sodium glutamate, potassium glutamate, ammonium glutamate and glutamic acid hydrochloride. The concentration of these in the medium is preferably 0.2-4.0% by weight as glutamic acid, and particularly preferably 0.4-1.0% by weight since this is superior for microbial growth and sporangium formation rate.

Nitrogen sources required for ordinary microbial culturing are preferably added to the medium used in the production process of the present invention in addition to glutamic acid. Examples of nitrogen sources include organic nitrogen sources normally used for culturing microorganisms such as peptones, meat extract, fish extract, lactoalbumin hydrolyzates and yeast extract. Examples of other nitrogen sources include inorganic nitrogen sources such as ammonia, nitric acid and their salts. The concentration of nitrogen sources in the medium used in the present invention is preferably 5.0% by weight or less, and more preferably 0.2-4.0% by weight since better microbial growth promotional effects are demonstrated.

Since the aforementioned organic nitrogen source contains various amino acids, the addition of said nitrogen source results in glutamic acid being effectively contained in the medium. Thus, although the concentration of glutamic acid is increased by increasing the amount of said nitrogen source added, sporangia containing spores and parasporal bodies cannot be formed effectively by this method. This is presumed to be because the concentrations of growth inhibitors and other unnecessary ingredients contained in the nitrogen source also similarly increase. Consequently, the ratio of glutamic acid to total amino acids in the medium is preferably 35-90% by weight.

However, total amino acids in the present invention refers to the collection of 16 types of free amino acids composed of alanine, arginine, aspartic acid, glutamic acid, glycine, isoleucine, leucine, lysine, methionine, phenylalanine, proline, serine, threonine, histidine, tyrosine and valine that are known to be contained in nitrogen sources such as peptones and yeast extract ordinarily used in media. The total amount of these 16 types of free amino acids is frequently used to roughly indicate the total amount of free amino acids contained in peptones, yeast extract and so forth.

Moreover, a carbon source normally required for microbial culturing may also be added to the medium used in the production process of the present invention. Examples of carbon sources include sugars such as trehalose and sucrose. In addition, agricultural waste products such as waste honey, starch degradation products and cheese whey can also be used. Although there are no particular restrictions on the concentration at which these carbon sources are added provided it is within a range at which the effects of the present invention are achieved, it is preferably 0.001-5% by weight with respect to the medium since this results in superior microbial growth promotional effects. However, since the presence of glucose is not preferable for forming sporangia containing spores and parasporal bodies, the concentration of glucose contained in the medium is preferably 0.01% by weight or less with respect to the medium.

Inorganic salts such as sodium salts or potassium salts such as potassium dihydrogenphosphate or dipotassium hydrogenphosphate may be added as necessary to the medium used in the production process of the present invention. Although there are no particular restrictions on the concentration of said added inorganic salt provided it is within a range at which the effects of the present invention are achieved, it is preferably 1% by weight or less with respect to the medium.

Moreover, microbial growth efficiency and sporangia formation rate can be further enhanced by adding pyruvic acid to the medium. The pyruvic acid referred to in the present invention also includes physiologically acceptable salts thereof. Examples of physiologically acceptable salts of pyruvic acid include sodium pyruvate and potassium pyruvate.

The concentration of pyruvic acid is preferably 0.01-0.5% by weight with respect to the medium, and particularly preferably 0.03-0.3% by weight since this concentration results in superior microbial growth efficiency and sporangia formation rate. The pyruvic acid may be mixed into the medium components before sterilization, may be sterilized separately from the medium components or may be added at the start of culturing.

The medium used in the production process of the present invention may be a liquid medium or a solid medium. In addition, a preferable example of a base material used when applying the production process of the present invention to a solid medium is a polysaccharide such as agar. The concentration of said base material in the medium is preferably 0.5-5% by weight, and particularly preferably 1-3% by weight since this concentration results in superior microbial growth promotional effects.

The suitable culturing temperature for the production process of the present invention is 25-32° C. In addition, the pH of the medium used in the production process of the present invention is preferably 6.5-8.5, and particularly preferably 7-8. Examples of methods for adjusting the pH of the medium include the addition of various buffers, the addition or routinely used acids such as hydrochloric acid or sulfuric acid, and the addition of routinely used bases such as sodium hydroxide, potassium hydroxide or ammonia.

Liquid culturing may be carried out by any method, examples of which include batch culturing, continuous culturing, semi-batch culturing and feeding culturing.

Although culturing time varies according to the culturing method, culture temperature, culture pH and inoculated microorganisms, it is normally 5-10 days in the case of batch culturing.

Following completion of culturing, sporangia containing spores and parasporal bodies are recovered from the culture. Since microbial cells containing said sporangia are present on the surface of the medium in the case of solid culturing, an example of a method for recovering the sporangia consists of washing off the microbial cells by suspending them by the addition of water, phosphate buffer or Tris-HCl of other buffer, followed by separating and recovering microbial cells by centrifugation, filtration or other typical separation method. On the other hand, in the case of a liquid culture, microbial cells containing sporangia are separated from the culture by centrifugation, filtration or other typical separation method to recover the microbial cells. In the case of the latter, a washing procedure may be added using water or buffer as necessary.

In the case of a culturing method using conventional media, sporangia of *Bacillus popilliae*, which contain spores and parasporal bodies that exhibit control effects on *Scarabaeidae* insects, are hardly obtained at all, and the sporangium formation rate represented with the following equation (ratio of the number of sporangia per number of microorganisms) is less than 0.05%.

Sporangia formation rate (%)=[(No. of sporangia)÷(No. of microorganisms)×100     (Equation 1)

In contrast, according to the production process of the present invention, sporangia of *Bacillus popilliae* containing spores and parasporal bodies can be produced at the high level of a sporangia formation rate of 5-50%. In addition, $5 \times 10^7$ or more, and normally $5 \times 10^7$ to $1 \times 10^9$, sporangia containing spores and parasporal bodies can be produced per 1 ml of liquid culture by liquid culturing.

Examples of microorganisms belonging to *Bacillus popilliae* that exhibit growth inhibitory or insecticidal activity against larva of *Scarabaeidae* insects include the bacterial species of *Bacillus popilliae Semadara*: FERM BP-8068, *Bacillus popilliae* var. *popilliae Mame*: FERM BP-8069, *Bacillus popilliae* var. *popilliae Hime*: FERM P-17660, *Bacillus popilliae* var. *popilliae Sakura*: FERM P-17662, *Bacillus popilliae* Dutky: ATCC No. 14706, and *Bacillus popilliae* subsp. *melolonthae*. Furthermore, *Bacillus popilliae Semadara* was deposited at the National Institute of Bioscience and Human-Technology, Agency of Industrial Science and Technology (currently the International Patent Organism Depository, National Institute of Advanced Industrial Science and Technology) on May 21, 1998 under the accession no. FERM P-16818, was transferred to international deposition based on the Budapest Treaty on Jun. 10, 2002, and assigned the accession no. FERM BP-8068. In addition, *Bacillus popilliae* var. *popilliae Mame* was deposited at the National Institute of Bioscience and Human-Technology, Agency of Industrial Science and Technology (currently the International Patent Organism Depository, National Institute of Advanced Industrial Science and Technology) on Nov. 25, 1999 under the accession no. FERM P-17661, was transferred to international deposition based on the Budapest Treaty on Jun. 10, 2002, and assigned the accession no. FERM BP-8069.

The sporangia of *Bacillus popilliae* containing spores and parasporal bodies obtained by the production process of the present invention exhibit control effects such as insecticidal activity or growth inhibition on larva of *Scarabaeidae* insects. Consequently, said sporangia are useful as a control agent of *Scarabaeidae* insects.

Examples of *Scarabaeidae* insects that can be controlled include *Anomala cuprea, Blitopertha orientalis, Popillia japonica, Phyllopertha diversa, Adoretus tenuimaculatus* and *Anomala rufocuprea*.

Sporangia of *Bacillus popilliae* containing spores and parasporal bodies produced according to the production process of the present invention may be used as a control agent for insects, and *Scarabaeidae* insects in particular, directly in the form of a liquid in which they are suspended. Alternatively, the sporangia may be dried and sprayed in the form of a powder. In addition, the sporangia may be dried followed by spraying as a suspension of water or buffer. Moreover, said sporangia may be formulated into a powder, granules, water-dispersible powder (water-entraining agent), emulsion, liquid, flowable preparation or spray (embrocation) in accordance with ordinary microbial agricultural chemical production methods together with various additives such as carriers, binders, dispersants, anti-freezing agents, thickeners or nutrients used in agricultural chemicals. In addition, sporangia of *Bacillus popilliae* containing spores and parasporal bodies obtained according to the production process of the present invention can also be used by mixing with other microbial preparations.

Although the content ratio of sporangia of *Bacillus popilliae* containing spores and parasporal bodies contained in the aforementioned control agent varies according to the form and usage method of the aforementioned control agent, normally it is preferably 0.0001-100% by weight.

The method for applying the control agent of the present invention is suitably selected according to the preparation form, usage method or target crop, examples of which include ground-level liquid spraying, ground-level solid spraying, aerial liquid spraying, aerial solid spraying, indoor application, soil mixing and soil perfusion. In addition, the control agent of the present invention can also be applied by mixing with other chemicals such as insecticides, nematocides, miticides, herbicides, bactericides, plant growth regulators, fertilizers and soil improvers (such as peat, humus and polyvinyl alcohol-based materials), or can be applied alternately or simultaneously with other chemicals without being mixed with them.

Although the applied amount of the aforementioned control agent cannot be specified unconditionally since it varies according to the type of *Scarabaeidae* insect, type of applied plant, preparation form and so forth, in the case of ground-level spraying, for example, the applied amount of sporangia of *Bacillus popilliae* containing spores and parasporal bodies of the present invention is preferably $10^{10}$-$10^{15}$ sporangia/are, and particularly preferably $10^{11}$-$10^{14}$ sporangia/are.

EXAMPLES

Although the following provides a more detailed explanation of the present invention through its examples and test examples, the scope of the present invention is not limited to these.

Reference Example 1

The free amino acid contents in the peptone, yeast extract and lactoalbumin hydrolyzate used as medium components of the media prepared in each example were measured by the post column method using orthophthalaldehyde (OPA).

(1) Sample Preparation

Mixed amino acid standard H (Wako Pure Chemical Industries, containing 2.5 mmol/l of each amino acid) used as the reference sample was diluted five-fold with 0.02 M hydrochloric acid and filtered with a filter having a pore size of 0.2 μm to prepare the reference sample solution.

Measurement samples were prepared by preparing 1.0% by weight solutions of each of Polypeptone S (Nippon Pharmaceutical) or Tryptone (Difco) as the peptone, and yeast extract manufactured by Oxoid or Difco as the yeast extract, and lactoalbumin hydrolyzate (Wako Pure Chemical Industries) followed by diluting these solutions two-fold with 10% by weight aqueous trichloroacetic acid solution, stirring well and centrifuging to remove any insoluble precipitates. Subsequently, the supernatant was filtered with a filter having a pore size of 0.2 μm to prepare the measurement sample solutions.

(2) Analysis

10 μl aliquots of the reference sample solution and measurement sample solutions were injected into a high-performance liquid chromatograph to analyze the amino acids. Furthermore, analyses were carried out using the Hitachi "LaChrom" Amino Acid Auto Analyzer based on the flow chart shown in FIG. 2. Furthermore, the compositions of the OPA labeling reaction solutions and eluates used in the amino acid analyses are shown in Tables 1 and 2, respectively.

TABLE 1

| Composition of OPA labeling reaction solution | R1 | R2 | R3 |
|---|---|---|---|
| Boric acid | | 21.6 g | 21.6 g |
| Sodium hydroxide | 24.0 g | | |
| 25% Brij-35 solution | | 4.0 ml | 4.0 ml |
| o-phthalaldehyde/methanol | | | 800 mg/ 10 ml |
| 2-mercaptoethanol | | | 2.0 ml |
| 5% sodium hypochlorite solution | | 150.0 μl | |
| Water | Remainder | Remainder | Remainder |
| Total volume | 1,000 ml | 1,000 ml | 1,000 ml |

Guaranteed reagents manufactured by Wako Pure Chemical Industries were used for all reagents.

TABLE 2

| Eluate composition | A | B | C |
|---|---|---|---|
| Sodium citrate $2H_2O$ | 8.14 g | 26.67 g | |
| Sodium chloride | 7.07 g | 54.35 g | |
| Citric acid $H_2O$ | 20.00 g | 6.10 g | |
| Sodium hydroxide | | | 8.0 g |
| Ethanol | 110 ml | | |
| Caprylic acid | 0.1 ml | 0.1 ml | 0.1 ml |
| Water | Remainder | Remainder | Remainder |
| Total | 1,000 ml | 1,000 ml | 1,000 ml |

Reagents manufactured by Wako Pure Chemical Industries were used for all reagents, and amino acid analytical grade reagents were used for the sodium citrate $2H_2O$, citric acid $H_2O$, and caprylic acid while guaranteed reagents were used for all others.

The concentrations of L-glutamic acid and total amino acids contained in each of the measurement sample solutions were calculated by converting from the peak areas obtained from the reference sample solution and each measurement sample solution, and those concentrations are shown in Table 3.

TABLE 3

|  | Peptone | | Yeast extract | | Lacto-albumin hydrolyzate |
|---|---|---|---|---|---|
|  | Polypeptone S | Tryptone | Oxoid | Difco | |
| Glutamic acid concentration (wt %) | 0.70 | 1.27 | 7.74 | 7.48 | 2.56 |
| Total amino acid concentration (wt %) | 17.88 | 21.65 | 36.67 | 31.45 | 27.37 |

Reference Example 2

In accordance with the culturing conditions described by Haynes, et al. (Journal of Invertebrate Pathology, Vol. 22, p. 377-381, 1973), namely 0.5 wt % peptone, 1.5 wt % yeast extract, 0.3 wt % dipotassium hydrogenphosphate, 0.1 wt % glucose and 1 wt % activated carbon, the glutamic acid concentrations and ratio of glutamic acid to total amino acids in media prepared by using all possible combinations of commercially available peptones and yeast extracts were calculated and shown in Table 4.

TABLE 4

| | Peptone and amount used | Yeast extract and amount used | Glutamic acid concentration in medium | Ratio of glutamic acid to total amino acids |
|---|---|---|---|---|
| No. 1 | 0.5 wt % Polypeptone S | 1.5 wt % Oxoid Yeast Extract | 0.12 wt % | 18.70 wt % |
| No. 2 | 0.5 wt % Polypeptone S | 1.5 wt % Difco Yeast Extract | 0.12 wt % | 20.62 wt % |
| No. 3 | 0.5 wt % Tryptone | 1.5 wt % Oxoid Yeast Extract | 0.12 wt % | 18.57 wt % |
| No. 4 | 0.5 wt % Tryptone | 1.5 wt % Difco Yeast Extract | 0.12 wt % | 20.44 wt % |

In the case of using commercially available peptone and yeast extract having highest glutamic acid contents, namely the Difco "Tryptone" and Oxoid "Yeast Extract", the glutamic acid concentration in the medium was 0.12% by weight.

In addition, the ratio of glutamic acid to total amino acids was a maximum of 20.62% by weight.

Preparation Example 1

0.5 g of L-glutamic acid (guaranteed reagent, Wako Pure Chemical Industries), 0.1 g activated carbon powder as absorbent (guaranteed reagent, Wako Pure Chemical Industries), 0.5 g of peptone ("Polypeptone S", Nippon Pharmaceutical), 0.5 g of yeast extract (Oxoid), 0.1 g of trehalose dihydrate (guaranteed reagent, Wako Pure Chemical Industries), and 2.0 g of agar (guaranteed reagent, Wako Pure Chemical Industries) were added to a flask containing 80 g of distilled water and mixed. Moreover, aqueous potassium hydroxide solution having a concentration of 1 mol/l was added while stirring to adjust the pH to 8.0. Moreover, distilled water was added to bring to a final weight of 100 g to prepare medium (A-1).

Preparation Example 2

Medium (A-2) was prepared in the same manner as Preparation Example 1 with the exception of using 2.0 g of "Diaion HP20" (trade name, adsorbent resin, Mitsubishi Chemical) instead of the activated carbon powder.

Comparative Preparation Example 1

Medium (B-1) was prepared in the same manner as Preparation Example 1 with the exception of not adding activated carbon powder.

Comparative Preparation Example 2

Medium (B-2) was prepared in the same manner as Preparation Example 1 with the exception of not adding L-glutamic acid in Preparation Example 1.

Comparative Preparation Example 3

Medium (B-3) was prepared in the same manner as Preparation Example 1 with the exception of using 2.0 g of "Diaion HP20" (trade name, absorbent resin, Mitsubishi Chemical) instead of activated carbon powder and not adding L-glutamic acid in Preparation Example 1.

Comparative Preparation Example 4

Medium (B-4) was prepared in the same manner as Preparation Example 1 with the exception of not adding activated carbon and L-glutamic acid in Preparation Example 1.

TABLE 5

| Medium Name | | A-1 | A-2 | B-1 | B-2 | B-3 | B-4 |
|---|---|---|---|---|---|---|---|
| Medium components | L-glutamic acid | 0.5 g | 0.5 g | 0.5 g | — | — | — |
| | Activated carbon | 0.1 g | — | — | 0.1 g | — | — |
| | Adsorbent resin | — | 2.0 g | — | — | 2.0 g | — |
| | Peptone | 0.5 g | 0.5 g | 0.5 g | 0.5 g | 0.5 g | 0.5 g |
| | Yeast extract | 0.5 g | 0.5 g | 0.5 g | 0.5 g | 0.5 g | 0.5 g |
| | Trehalose dihydrate | 0.1 g | 0.1 g | 0.1 g | 0.1 g | 0.1 g | 0.1 g |
| | Agar | 2.0 g | 2.0 g | 2.0 g | 2.0 g | 2.0 g | 2.0 g |
| | Distilled water | Rem. | Rem. | Rem. | Rem. | Rem. | Rem. |
| Total Amount | | 100 g | 100 g | 100 g | 100 g | 100 g | 100 g |

The glutamic acid concentration in the medium and the ratio of glutamic acid to total amino acids were respectively determined based on Reference Example 1, and those results are shown in Tables 6 and 7.

Examples 1-2 and Comparative Examples 1-4

Each of the media obtained in the aforementioned Preparation Examples 1-2 and Comparative Preparation Examples 1-4 was sterilized in an autoclave for 20 minutes at 121° C., and 20 ml aliquots were poured into plastic Petri dishes having a diameter of 9 cm while stirring well before the agar solidified to prepare media plates.

Sporangia of *Bacillus popilliae Semadara* and *Bacillus popilliae* var. *popilliae Sakura* were collected, as inoculum, from the larva of *Scarabaeidae* insects infected with milky disease. The numbers of sporangia were measured by examining directly with a microscope, and sporangia liquids were prepared with distilled water so that the concentration of sporangia was $1 \times 10^7$ sporangia/ml. 0.5 ml of these liquids were then transferred to a plastic tube followed by heat treatment for 20 minutes at 70° C. using a heating block. 50 μl of the sporangia liquid were applied to the media plates prepared as described above followed by culturing for 8 days in an incubator at 30° C.

Following completion of culturing, those Petri dishes free of contaminating bacteria were selected followed by dropping in 2 ml of distilled water to thoroughly suspend the resulting colonies and recover the microbial cells. The numbers of sporangia and microbial cells were measured by direct microscopic examination followed by calculation of the sporangia formation rate. The number of sporangia per Petri dish and sporangia formation rate are shown for each strain in Tables 6 and 7.

TABLE 6

Culture of *Bacillus popilliae Semadara*

| Medium Name | Glutamic acid in culture liquid (wt %) | Ratio of glutamic acid to total amino acids (wt %) | No. of sporangia (sporangia/ Petri dish) | Sporangia formation rate (%) |
|---|---|---|---|---|
| A-1 | 0.54 | 70.16 | $2.5 \times 10^9$ | 42 |
| A-2 | 0.54 | 70.16 | $1.0 \times 10^9$ | 37 |
| B-1 | 0.54 | 70.16 | 0 | 0 |
| B-2 | 0.04 | 15.47 | $5.0 \times 10^8$ | 13 |
| B-3 | 0.04 | 15.47 | $2.0 \times 10^8$ | 11 |
| B-4 | 0.04 | 15.47 | 0 | 0 |

TABLE 7

Culture of *Bacillus popilliae* var. *popilliae Sakura*

| Medium Name | Glutamic acid in culture liquid (wt %) | Ratio of glutamic acid to total amino acids (wt %) | No. of sporangia (sporangia/ Petri dish) | Sporangia formation rate (%) |
|---|---|---|---|---|
| A-1 | 0.54 | 70.16 | $3.5 \times 10^9$ | 40 |
| A-2 | 0.54 | 70.16 | $2.0 \times 10^9$ | 25 |
| B-1 | 0.54 | 70.16 | 0 | 0 |
| B-2 | 0.04 | 15.47 | $1.0 \times 10^8$ | 18 |
| B-3 | 0.04 | 15.47 | $7.0 \times 10^8$ | 9 |
| B-4 | 0.04 | 15.47 | 0 | 0 |

Based on the results of Tables 6 and 7, culturing in media containing adsorbent and glutamic acid resulted in higher numbers of sporangia and sporangia formation rates for both strains.

Preparation Example 3

5 g of L-glutamic acid (guaranteed reagent, Wako Pure Chemical Industries), 5 g of peptone ("Polypeptone S", Nippon Pharmaceutical), 5 g of yeast extract (Oxoid) and 5 g of trehalose dihydrate (guaranteed reagent, Wako Pure Chemical Industries) were added to a beaker containing 700 g of distilled water and mixed. After adjusting the pH to 7.6 by adding aqueous potassium hydroxide solution having a concentration of 5 mol/l while stirring, distilled water was added to bring to a final weight of 850 g. This was then transferred to a fermentation tank equipped with a pH electrode (B. E. Marubishi) and sterilized by autoclaving for 60 minutes at 121° C.

Next, 3 g of activated carbon powder (guaranteed reagent, Wako Pure Chemical Industries) were placed in a flask followed by the addition of distilled water to bring to a final weight of 100 g to prepare an activated carbon dispersion. In addition, 1 g of antifoaming agent (Disfoam CA-123, NOF) was placed in a different flask followed by the addition of distilled water to bring to a final weight of 50 g to prepare an antifoaming agent liquid. The activated carbon dispersion and antifoaming agent liquid were sterilized followed by their aseptic addition to the fermentation tank to prepare medium (C-1).

Comparative Preparation Example 5

Medium (D-1) was prepared in the same manner as Preparation Example 3 with the exception of not adding activated carbon powder in Preparation Example 3.

Comparative Preparation Example 6

Medium (D-2) was prepared in the same manner as Preparation Example 3 with the exception of not adding L-glutamic acid in Preparation Example 3.

Comparative Preparation Example 7

Medium (D-3) was prepared in the same manner as Preparation Example 3 with the exception of using 5 g of L-alanine (guaranteed reagent, Wako Pure Chemical Industries) instead of L-glutamic acid in Preparation Example 3.

TABLE 8

| | Medium Name | C-1 | D-1 | D-2 | D-3 |
|---|---|---|---|---|---|
| Medium compo- nents | L-glutamic acid | 5 g | 5 g | — | — |
| | L-alanine | — | — | — | 5 g |
| | Activated carbon | 3 g | — | 3 g | 3 g |
| | Peptone | 5 g | 5 g | 5 g | 5 g |
| | Yeast extract | 5 g | 5 g | 5 g | 5 g |
| | Trehalose dihydrate | 5 g | 5 g | 5 g | 5 g |
| | Antifoaming agent | 1 g | 1 g | 1 g | 1 g |
| | Distilled water | Rem. | Rem. | Rem. | Rem. |
| | Total Amount | 1,000 g | 1,000 g | 1,000 g | 1,000 g |

Comparative Preparation Example 8

0.5 g of peptone ("Tryptone", Difco), 1.5 g of yeast extract (Oxoid), 0.3 g of dipotassium hydrogenphosphate (guaranteed reagent, Wako Pure Chemical Industries), 0.1 g of glucose (guaranteed reagent, Wako Pure Chemical Industries) and 1.0 g of activated carbon powder (guaranteed reagent, Wako Pure Chemical Industries) were added to a flask containing 80 g of distilled water and mixed in order to compare with the findings of Haynes, et al. (Journal of Invertebrate Pathology, Vol. 22, p. 377-381, 1973). Moreover, distilled water was added to bring to a final weight of 100 g. This was then sterilized using an autoclave for 20 minutes at 121° C. to prepare medium (D-4).

TABLE 9

| | Medium Name | D-4 |
|---|---|---|
| Medium components | Activated carbon | 1.0 g |
| | Tryptone | 0.5 g |
| | Yeast extract | 1.5 g |
| | Glucose | 0.1 g |
| | Dipotassium hydrogenphosphate | 0.3 g |
| | Distilled water | Remainder |
| | Total Amount | 100 g |

Example 3 and Comparative Examples 5-8

Sporangia produced in advance by culturing *Bacillus popilliae Semadara*, *Bacillus popilliae* var. *popilliae Sakura* and *Bacillus popilliae* var. *popilliae Mame* using medium (A-1) containing activated carbon were used as inoculum. The aseptically collected sporangia were measured by direct microscopic examination and sporangia liquids were prepared with distilled water so that the concentrations of sporangia were $1 \times 10^9$ sporangia/ml.

1 ml aliquots of the sporangia liquid of each strain were transferred to plastic tubes followed by heat treatment for 20 minutes at 70° C. using a heating block. 1 ml of each sporangia liquid was inoculated into media (C-1) and (D-1) through (D-3) in the aforementioned fermentation tank (B. E. Marubishi) followed by culturing for 7 days under controlled conditions of aeration of 1 vvm, 30° C. and pH 7.6 while stirring the liquid medium by rotating the stirrer provided with the fermentation tank at 150 rpm. On the other hand, 0.01 ml of sporangia liquid was inoculated into medium (D-4) followed by culturing for 7 days in the same manner with the exception of making the rotating speed of the stirrer provided with the fermentation tank 100 rpm within an incubator at 30° C.

Following completion of culturing, the numbers of sporangia and microbial cells per unit volume in the liquid cultures were measured by direct microscopic examination followed by calculation of the sporangia formation rate. The numbers of sporangia per 1 ml of liquid culture and sporangia formation rates are shown in Tables 10 through 12.

TABLE 10

Culture of *Bacillus popilliae Semadara*

| Medium Name | Glutamic acid concentration in liquid culture (wt %) | Ratio of glutamic acid to total amino acids (wt %) | No. of sporangia (sporangia/ml) | Sporangia formation rate (%) |
|---|---|---|---|---|
| C-1 | 0.54 | 70.16 | $1.2 \times 10^8$ | 6.0 |
| D-1 | 0.54 | 70.16 | 0 | 0 |
| D-2 | 0.04 | 15.47 | 0 | 0 |
| D-3 | 0.04 | 5.76 | 0 | 0 |
| D-4 | 0.12 | 18.60 | 0 | 0 |

TABLE 11

Culture of *Bacillus popilliae* var. *popilliae Sakura*

| Medium Name | Glutamic acid concentration in liquid culture (wt %) | Ratio of glutamic acid to total amino acids (wt %) | No. of sporangia (sporangia/ml) | Sporangia formation rate (%) |
|---|---|---|---|---|
| C-1 | 0.54 | 70.16 | $1.5 \times 10^8$ | 6.8 |
| D-1 | 0.54 | 70.16 | 0 | 0 |
| D-2 | 0.04 | 15.47 | 0 | 0 |
| D-3 | 0.04 | 5.76 | 0 | 0 |
| D-4 | 0.12 | 18.60 | 0 | 0 |

TABLE 12

Culture of *Bacillus popilliae* var. *popilliae Mame*

| Medium Name | Glutamic acid concentration in liquid culture (wt %) | Ratio of glutamic acid to total amino acids (wt %) | No. of sporangia (sporangia/ml) | Sporangia formation rate (%) |
|---|---|---|---|---|
| C-1 | 0.54 | 70.16 | $1.6 \times 10^8$ | 7.2 |
| D-1 | 0.54 | 70.16 | 0 | 0 |
| D-2 | 0.04 | 15.47 | 0 | 0 |
| D-3 | 0.04 | 5.76 | 0 | 0 |
| D-4 | 0.12 | 18.60 | 0 | 0 |

Based on the results of Tables 10 through 12, it is clear that sporangia are obtained only from media containing adsorbent and glutamic acid.

Preparation Example 4

0.2 g of L-glutamic acid (guaranteed reagent, Wako Pure Chemical Industries), 7.5 g of peptone ("Polypeptone S", Nippon Pharmaceutical), 7.5 g of yeast extract (Oxoid), 5 g of lactoalbumin hydrolyzate (Wako Pure Chemical Industries) and 5 g of trehalose dehydrate (guaranteed reagent, Wako Pure Chemical Industries) were added to a beaker containing 700 g of distilled water and mixed. After adjusting the pH to 7.6 by adding aqueous potassium hydroxide solution having a concentration of 5 mol/l while stirring, distilled water was added to bring to a final weight of 850 g. This was then transferred to a fermentation tank equipped with a pH electrode (B. E. Marubishi) and sterilized by autoclaving for 60 minutes at 121° C.

Next, 3 g of activated carbon powder (guaranteed reagent, Wako Pure Chemical Industries) were placed in a flask followed by the addition of distilled water to bring to a final weight of 100 g to prepare an activated carbon dispersion. In addition, 1 g of antifoaming agent (Disfoam CA-123, NOF) was placed in a flask followed by the addition of distilled water to bring to a final weight of 50 g to prepare an antifoaming agent liquid. The activated carbon dispersion and antifoaming agent liquid were sterilized followed by their aseptic addition to each fermentation tank to prepare medium (E-1).

Preparation Examples 5-8

Media (E-2) through (E-5) were respectively prepared in the same manner as Preparation Example 4 with the exception of making the amounts of L-glutamic acid added 0.5 g, 0.8 g, 1.5 g and 3.0 g, respectively.

Comparative Preparation Example 9

Medium (F-1) was prepared in the same manner as Preparation Example 4 with the exception of not adding L-glutamic acid.

Comparative Preparation Example 10

Medium (F-2) was prepared in the same manner as Preparation Example 4 with the exception of making the amount of L-glutamic acid added 5.0 g.

TABLE 13

| | Medium Name | F-1 | E-1 | E-2 | E-3 | E-4 | E-5 | F-2 |
|---|---|---|---|---|---|---|---|---|
| Medium components | L-glutamic acid | — | 0.2 g | 0.5 g | 0.8 g | 1.5 g | 3.0 g | 5.0 g |
| | Activated carbon | 3 g | 3 g | 3 g | 3 g | 3 g | 3 g | 3 g |
| | Peptone | 7.5 g | 7.5 g | 7.5 g | 7.5 g | 7.5 g | 7.5 g | 7.5 g |
| | Yeast extract | 7.5 g | 7.5 g | 7.5 g | 7.5 g | 7.5 g | 7.5 g | 7.5 g |
| | Lactoalbumin hydrolyzate | 5.0 g | 5.0 g | 5.0 g | 5.0 g | 5.0 g | 5.0 g | 5.0 g |
| | Trehalose dihydrate | 5.0 g | 5.0 g | 5.0 g | 5.0 g | 5.0 g | 5.0 g | 5.0 g |
| | Agar | 1 g | 1 g | 1 g | 1 g | 1 g | 1 g | 1 g |
| | Distilled water | Rem. | Rem. | Rem. | Rem. | Rem. | Rem. | Rem. |
| Total Amount | | | | | 1,000 g | | | |

Examples 4-8 and Comparative Examples 9-10

Sporangia produced in advance by culturing *Bacillus popilliae Semadara* using medium (A-1) containing activated carbon were used as inoculum. The aseptically collected sporangia were measured by direct microscopic examination and a sporangia liquid was prepared with distilled water so that the concentration of sporangia was $1 \times 10^9$ sporangia/ml.

1 ml aliquots of the sporangia liquid were transferred to plastic tubes followed by heat treatment for 20 minutes at 70° C. using a heating block. 1 ml each of the sporangia liquid was inoculated into media (E-1) through (E-5) and (F-1) through (F-2) in the aforementioned fermentation tank (B. E. Marubishi) followed by culturing for 7 days under controlled conditions of aeration of 1 vvm, 30° C. and pH 7.6 while stirring the liquid medium by rotating the stirrer provided with the fermentation tank at 150 rpm.

Figure 3:
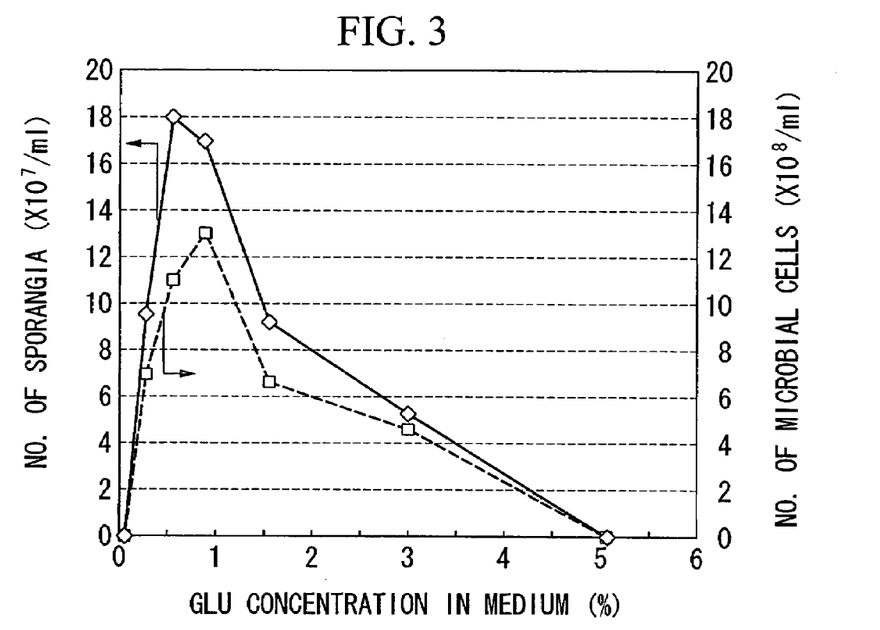

Following completion of culturing, the numbers of sporangia and microbial cells per unit volume in the liquid cultures were measured by direct microscopic examination followed by calculation of the sporangia formation rate according to the equation 1. The numbers of microbial cells and numbers of sporangia per 1 ml of liquid culture along with the sporangia formation rates are shown in Table 14. In addition, the relationship between glutamic acid concentration with respect to the medium (wt %) and the number of microbial cells ($\times 10^8$ cells/ml) and number of sporangia ($\times 10^7$ sporangia/ml) is shown in FIG. 3.

Preparation Example 9

5 g of L-glutamic acid (guaranteed reagent, Wako Pure Chemical Industries), 1 g of sodium pyruvate (guaranteed reagent, Wako Pure Chemical Industries), 7.5 g of peptone ("Polypeptone S", Nippon Pharmaceutical), 7.5 g of yeast extract (Oxoid), 5 g of lactoalbumin hydrolyzate (Wako Pure Chemical Industries) and 5 g of trehalose dihydrate (guaranteed reagent, Wako Pure Chemical Industries) were added to a beaker containing 700 g of distilled water and mixed. After adjusting the pH to 7.6 by adding aqueous sodium hydroxide solution having a concentration of 4 mol/l while stirring, distilled water was added to bring to a final weight of 850 g. This was then transferred to a fermentation tank equipped with a pH electrode (B. E. Marubishi) and sterilized by autoclaving for 50 minutes at 121° C.

Next, 2.5 g of activated carbon powder (guaranteed reagent, Wako Pure Chemical Industries) were placed in a flask followed by the addition of distilled water to bring to a final weight of 100 g to prepare an activated carbon dispersion. In addition, 1 g of antifoaming agent (Disfoam CA-123, NOF) was placed in a different flask followed by the addition of distilled water to bring to a final weight of 50 g to prepare an antifoaming agent liquid. The activated carbon dispersion and antifoaming agent liquid were sterilized followed by their aseptic addition to the fermentation tank to prepare medium (G-1).

Preparation Example 10

Medium (G-2) was prepared in the same manner as Preparation Example 9 with the exception of making the amount of sodium pyruvate added 2.5 g.

TABLE 14

Culture of *Bacillus popilliae Semadara*

| Medium Name | Glutamic acid concentration in liquid culture (wt %) | Ratio of glutamic acid to total amino acids (wt %) | No. of microbial cells (cells/ml) | No. of sporangia (sporangia/ml) | Sporangia formation rate (%) |
|---|---|---|---|---|---|
| F-1 | 0.08 | 13.94 | $5.8 \times 10^8$ | 0 | 0 |
| E-1 | 0.28 | 37.01 | $6.9 \times 10^8$ | $9.6 \times 10^7$ | 14.0 |
| E-2 | 0.58 | 55.08 | $1.1 \times 10^8$ | $1.8 \times 10^8$ | 17.0 |
| E-3 | 0.88 | 65.09 | $1.3 \times 10^8$ | $1.7 \times 10^8$ | 12.7 |
| E-4 | 1.58 | 77.03 | $6.8 \times 10^8$ | $9.2 \times 10^7$ | 13.5 |
| E-5 | 3.08 | 86.75 | $4.6 \times 10^8$ | $5.2 \times 10^7$ | 11.2 |
| F-2 | 5.08 | 91.53 | $3.5 \times 10^8$ | 0 | 0 |

Comparative Preparation Example 11

Medium (H-1) was prepared in the same manner as Preparation Example 9 with the exception of not adding L-glutamic acid.

TABLE 15

| Medium Name | | G-1 | G-2 | H-1 |
|---|---|---|---|---|
| Medium components | L-glutamic acid | 5 g | 5 g | — |
| | Sodium pyruvate | 1 g | 2.5 g | 1 g |
| | Activated carbon | 2.5 g | 2.5 g | 2.5 g |
| | Peptone | 7.5 g | 7.5 g | 7.5 g |
| | Yeast extract | 7.5 g | 7.5 g | 7.5 g |
| | Lactoalbumin hydrolyzate | 5 g | 5 g | 5 g |
| | Trehalose dihydrate | 5 g | 5 g | 5 g |
| | Antifoaming agent | 1 g | 1 g | 1 g |
| | Distilled water | Remainder | Remainder | Remainder |
| Total Amount | | 1,000 g | 1,000 g | 1,000 g |

Examples 9-10 and Comparative Example 11

Using *Bacillus popilliae Semadara* in the same manner as Example 6, 1 ml aliquots of sporangia liquid were aseptically inoculated into media (G-1) through (G-2) and medium (H-1) in the aforementioned fermentation tank (B. E. Marubishi) followed by the start of culturing. The culturing conditions consisted of a temperature of 29° C., aeration of 0.5 vvm and stirring at 150 rpm using the stirrer provided with the fermentation tank. During culturing, the pH was controlled to pH 7.6 with aqueous sodium hydroxide solution having a concentration of 4 mol/l and sulfuric acid having a concentration of 4 mol/l.

Culturing was carried out for 5 days and the numbers of sporangia and microbial cells per unit volume in the liquid cultures were measured by direct microscopic examination followed by calculation of the sporangia formation rate. The numbers of microbial cells and numbers of sporangia per 1 ml of liquid culture along with the sporangia formation rates are shown in Table 16.

TABLE 16

| Medium Name | Glutamic acid concentration in liquid culture (wt %) | Ratio of glutamic acid to total amino acids (wt %) | Pyruvic acid concentration (wt %) | No. of microbial cells (cells/ml) | No. of sporangia (sporangia/ml) | Sporangia formation rate (%) |
|---|---|---|---|---|---|---|
| G-1 | 0.58 | 55.08 | 0.08 | $1.5 \times 10^8$ | $2.5 \times 10^8$ | 16.7 |
| G-2 | 0.58 | 55.08 | 0.20 | $1.6 \times 10^8$ | $4.8 \times 10^8$ | 30.0 |
| H-1 | 0.08 | 15.47 | 0.08 | $1.0 \times 10^8$ | 0 | 0 |

Based on the results shown in Table 16, the addition of sodium pyruvate resulted in an increase in the sporangia formation rate, and resulting number of sporangia were also found to increase.

Biological Test Example 1

A test was conducted on the insecticidal and growth inhibitory effects on larva of *Scarabaeidae* insects of sporangia containing spores and parasporal bodies, spores and parasporal bodies of *Bacillus popilliae Semadara*.

Sporangia of *Bacillus popilliae Semadara* acquired in medium using medium (A-1) of Example 1 were suspended in distilled water to $2 \times 10^8$ sporangia/ml to prepare suspension (I). Moreover, a suspension containing sporangia of *Bacillus popilliae Semadara* acquired in medium using medium (A-1) of Example 1 was treated with a French press to separate and remove the spores and parasporal bodies from the sporangia. The separated spores were suspended in distilled water to $2 \times 10^8$ spores/ml to prepare suspension (II). In addition, the separated parasporal bodies were suspended in distilled water to $2 \times 10^8$ parasporal bodies/ml to prepare suspension (III).

Eighty plastic cups were prepared having a diameter of 6 cm and filled with about 20 g each of leaf mold.

(i) Suspension (I) containing sporangia was sprayed onto the 20 plastic cups so that the number of sporangia was $2 \times 10^8$ sporangia/cup.

(ii) Suspension (II) containing spores only was sprayed onto the 20 plastic cups so that the number of spores was $2 \times 10^8$ spores/cup.

(iii) Suspension (III) containing parasporal bodies only was sprayed onto 20 plastic cups so that the number of parasporal bodies was $2 \times 10^8$ parasporal bodies/cup.

(iv) Nothing was sprayed onto the remaining 20 cups and these cups were used as a control test.

One second instar larva each of *Anomala cuprea* was placed in each cup and bred for 30 days in an incubator at 25° C. followed by measuring the mortality rates and average body weight increase of the surviving larva over time. The cumulative mortality rates are shown in Table 17, while the results for growth inhibitory effects are shown in FIG. 4.

TABLE 17

| | Cumulative Mortality Rates (%) | | |
|---|---|---|---|
| Test Group | Day 11 | Day 23 | Day 30 |
| (i) | 20 | 40 | 45 |
| (ii) | 0 | 5 | 10 |
| (iii) | 15 | 20 | 25 |
| Control | 0 | 0 | 0 |

Figure 4:
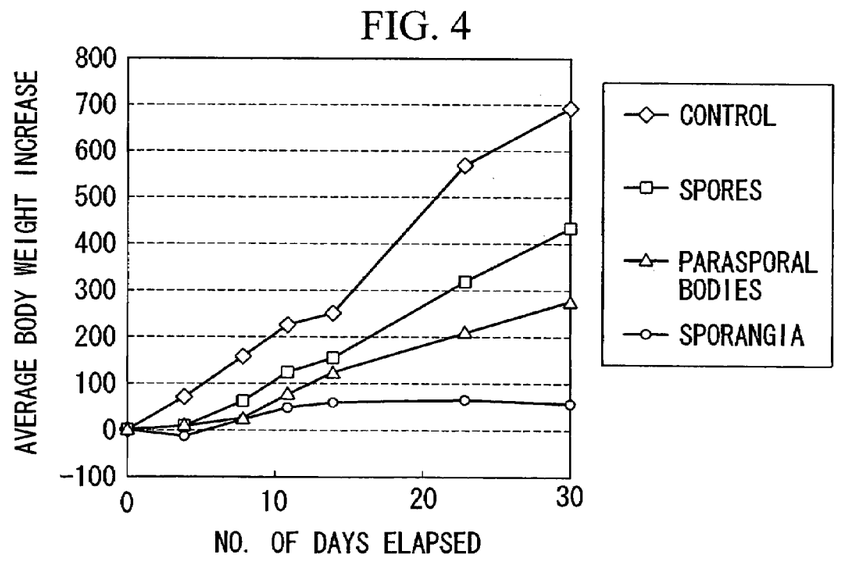
FIG. 4 is a graph showing the growth inhibitory effects of *Anomala cuprea* in Biological Test Example 1.

Based on the results shown in Table 17 and FIG. 4, sporangium of *Bacillus popilliae* containing both spores and parasporal bodies were confirmed to demonstrate superior insecticidal and larva growth inhibitory effects.

Biological Test Example 2

A test was conducted of the insecticidal activity on *Scarabaeidae* insects by sporangia obtained according to the production process (solid culturing) of the present invention.

Sporangia of *Bacillus popilliae Semadara* acquired in medium using activated carbon-containing plate medium (A-1) of Example 1 were suspended in distilled water to $1 \times 10^9$ sporangia/ml to prepare a sporangia liquid. Approximately 20 g each of leaf mold were laced in 40 plastic cups having a diameter of 6 cm, and the sporangia liquid was sprayed onto 20 of those cups so that the number of sporangia was $1 \times 10^9$ sporangia/cup. Sporangia liquid was not sprayed onto the remaining 20 cups and these cups were used for a control test. One second instar larva each of *Anomala cuprea* was placed in each cup and bred for 40 days in an incubator at 25° C. followed by investigating the number of insects that died over time to determine the cumulative mortality rates (%). Those results are shown in Table 18.

TABLE 18

| Test Group | Cumulative Mortality Rates (%) | | | |
|---|---|---|---|---|
| | Day 10 | Day 20 | Day 30 | Day 40 |
| Control | 0 | 0 | 0 | 0 |
| Sporangia Addition | 40 | 60 | 90 | 100 |

Based on the results shown in Table 18, a mortality rate of 100% was observed on day 40 in the test group in which sporangia of *Bacillus popilliae* containing spores and parasporal bodies of the present invention were sprayed.

Biological Test Example 3

A test was conducted of the insecticidal activity on *Scarabaeidae* insects by sporangia obtained according to the production process (liquid culturing) of the present invention.

The test groups were prepared in the same manner as Biological Test Example 2. However, the sprayed sporangia consisted of:

(i) sporangia of *Bacillus popilliae Semadara* acquired in medium using activated carbon-containing liquid medium (C-1) of Example 3, and (ii) sporangia of *Bacillus popilliae* var. *popilliae Mame* acquired in medium using activated carbon-containing liquid medium (C-1) of Example 3.

One second instar larva each of *Anomala cuprea* was placed in each cup and bred for 40 days in an incubator at 25° C. followed by investigating the number of insects that died over time to determine the cumulative mortality rates (%). The insecticidal activity on *Anomala cuprea* of sporangia obtained in liquid culturing of the present invention is shown in Table 19.

TABLE 19

| Test Group | Cumulative Mortality Rates (%) | | | |
|---|---|---|---|---|
| | Day 10 | Day 20 | Day 30 | Day 40 |
| Control | 0 | 0 | 0 | 0 |
| (i) | 15 | 30 | 95 | 100 |
| (ii) | 10 | 35 | 65 | 85 |

Based on the results shown in Table 19, a mortality rate of 85-100% was observed on day 40 in the test groups in which sporangia of *Bacillus popilliae* containing spores and parasporal bodies of the present invention were sprayed.

Biological Test Example 4

A test was conducted of the insecticidal activity on *Scarabaeidae* insects by sporangia obtained according to the production process (liquid culturing) of the present invention. Sporangia of *Bacillus popilliae Semadara* obtained by culturing in medium (G-2) shown in Example 10 were suspended in distilled water to $1 \times 10^9$ sporangia/ml to prepare a sporangia liquid.

Approximately 20 g each of leaf mold were laced in 40 plastic cups having a diameter of 6 cm. The sporangia liquid was sprayed onto 20 of those cups so that the number of sporangia was $1 \times 10^9$ sporangia/cup. Sporangia liquid was not sprayed onto the remaining 20 cups and these cups were used for a control test. One second instar larva each of *Anomala cuprea* was placed in each cup and bred for 40 days in an incubator at 25° C. followed by investigating the number of insects that died over time to determine the cumulative mortality rates (%). Those results are shown in Table 20.

TABLE 20

| Test Group | Cumulative Mortality Rates (%) | | | |
|---|---|---|---|---|
| | Day 10 | Day 20 | Day 30 | Day 40 |
| Control | 0 | 0 | 0 | 0 |
| Sporangia Addition | 15 | 30 | 95 | 100 |

Based on the results shown in Table 20, a mortality rate of 100% was observed on day 40 in the test group in which sporangia of *Bacillus popilliae* containing spores and parasporal bodies of the present invention were sprayed.

What is claimed is:

1. A process for producing sporangia of *Bacillus popilliae* containing spores and parasporal bodies comprising the steps of:
   culturing *Bacillus popilliae* in a medium containing an adsorbent and 0.2-4.0% by weight of free glutamic acid so that the ratio of glutamic acid to total amino acids contained in the medium is within the range of 35 to 90% by weight, and
   recovering the sporangia from the medium.

2. A process for producing sporangia of *Bacillus popilliae* according to claim 1, wherein the medium further contains pyruvic acid.

3. A process for producing sporangia of *Bacillus popilliae* according to claim 2, wherein the ratio of pyruvic acid in the medium is within the range of 0.01 to 0.5% by weight.

* * * * *